United States Patent [19]

Libby

[11] 4,432,975
[45] Feb. 21, 1984

[54] PROCESS FOR INTRODUCING VITAMIN B-12 INTO THE BLOODSTREAM

[75] Inventor: Alfred F. Libby, Fullerton, Calif.

[73] Assignee: ICN Pharmaceuticals, Inc., Covina, Calif.

[21] Appl. No.: 312,398

[22] Filed: Oct. 19, 1981

Related U.S. Application Data

[63] Continuation-in-part of Ser. No. 253,712, Apr. 13, 1981, abandoned.

[51] Int. Cl.$^3$ .............................................. A61K 31/68
[52] U.S. Cl. .................................................... 424/201
[58] Field of Search ......................................... 424/201

[56] References Cited

U.S. PATENT DOCUMENTS

| 3,060,095 | 10/1962 | Stolar | 424/201 |
| 3,160,565 | 12/1964 | Duell | 424/201 |
| 3,175,948 | 3/1965 | Koff et al. | 424/201 |
| 3,384,546 | 5/1968 | Palermo | 424/201 |
| 3,424,842 | 1/1969 | Nürnberg | 424/201 |
| 3,870,790 | 3/1975 | Lowey et al. | 424/201 |

Primary Examiner—Douglas W. Robinson
Attorney, Agent, or Firm—Lyon & Lyon

[57] ABSTRACT

A process for introducing vitamin B-12 into the bloodstream is disclosed by which vitamin B-12 is absorbed sublingually. The vitamin B-12 is in the form of a microlozenge which contains cyanocobalamin or hydroxocobalamin and which is capable of being dissolved in approximately four minutes or less.

13 Claims, No Drawings

PROCESS FOR INTRODUCING VITAMIN B-12 INTO THE BLOODSTREAM

CROSS REFERENCE TO RELATED APPLICATIONS

This is a continuation-in-part of U.S. Ser. No. 253,712 filed Apr. 13, 1981, now abandoned entitled "Composition and Method for Treating Alcohol and Drug Addicts", which is hereby incorporated by reference.

BACKGROUND OF THE INVENTION

It is now well understood and accepted that Vitamin B-12 is an important and central factor in many body functions. It is necessary for normal metabolism of nerve tissue and is involved in protein, fat and carbohydrate metabolism. Vitamin B-12 is required for the synthesis and transfer of single carbon units such as the methyl group, and aids in the synthesis of methionine and choline, which are important lipotrophic substances.

Among its other functions, Vitamin B-12 is required for the formation of red blood cells and increases tissue deposition of Vitamin A by improving either carotene absorption or its conversion to Vitamin A. Vitamin B-12 is also closely related to the actions of four amino acids, pantothenic acid, and Vitamin C, and plays a part in reproduction and lactation. Additionally, vitamin B-12 helps reduce the possibility of skin bruises and has been suggested as helpful in combatting alcoholism, diabetes mellitus, osteoarthritis, multiple sclerosis, certain mental diseases, and a number of other diseases and abnormalities.

Vitamin B-12, however, is a very complex vitamin. It contains an atom of cobalt in its center and is a charged molecule with a high molecular weight. The structure is similar to that of hemoglobin with iron at its center and to chlorophyll with a central magnesium atom. It cannot be made synthetically, but must be grown, like penicillin, in bacteria or molds. Animal protein is virtually the only source in which vitamin B-12 occurs naturally in substantial quantities. The human body cannot synthesize vitamin B-12, and consequently, it must be obtained externally if there is a deficiency, that is, by dietary intake.

The nature of vitamin B-12 is such that it is transported throughout the body by serum protein in the blood and is stored by many of the body tissues, especially the liver, kidney, stomach, muscle and brain. The liver is the primary storage site, and in good nutritional states, contains about 2 to 5 milligrams, which is considered sufficient to last the average human being from about 2 to 5 years.

For vitamin B-12 to be effective within the human body, a special system is necessary, since, due to its complex structure, it is unable to diffuse across cell membranes as are other vitamins. This special system is called the "intrinsic factor" and is a special protein secreted by the stomach. The intrinsic factor, by a mechanism not entirely understood, transports vitamin B-12 across the cell membrane in the wall of the small intestine, with the vitamin B-12 being released from the intrinsic factor and asorbed into the blood.

When the human body is healthy, the amount of vitamin B-12 ordinarily absorbed into the blood by the intrinsic factor is about 2.5 to 3 micrograms per day. However, when the human body is not healthy and is suffering from pernicious anemia, for example, the intrinsic factor is lacking, and consequently, the body does not absorb adequate amounts of vitamin B-12. The vitamin B-12 deficiency manifests itself in human beings, most commonly, in motor and mental difficulties. The symtoms are rapid heartbeat, cardiac pain, shortness of breath, edema of the face, general jaundice and intense brown discoloration around the small joints, weakness and fatigue. Neurological changes, such as peripheral neuritis, spinal cord changes, intermittent numbness and tinglings in arms and legs, diminished tendon reflexes, unsteady gait, etc. may also occur.

To overcome such deficiency, however, is extremely difficult since vitamin B-12 does not become absorbed into the blood to any significant extent when taken orally, regardless of the amount. Thus, as reported by H. Berlin et al, *Acta Med. Scand.* 184 247–258, 1968, and H. Hedstrand, *Acta Med. Scand.* 186 535–537, 1969, only approximately 1.2% of oral vitamin B-12 is absorbed over rather a wide range and such absorption rate is not dependent on the presence of the intrinsic factor. Moreover, even insofar as the absorption of such a small quantity is concerned, there may be significant limitations such as a lack of hydrochloric acid, a lack of animal protein intake, or other gastro intestinal problems which create poor absorption capabilities.

Because of the extremely limited ability of vitamin B-12 to be absorbed into the blood when taken orally, in the past, the treatment process has had to be in the form of vitamin B-12 injections. Such injections, however, have a number of significant drawbacks. First, injections are objectionable to administer because of the pain associated therewith. In this same regard, to many, the idea of injection treatments is inherently objectionable and offensive, and, consequently, there is a tendency not to proceed with the treatment. Additionally, as with any injection treatment process, needle abscess may occur and the treatment process is expensive. Finally, in the treatment of persons addicted to narcotics, with which pernicious anemia is often associated, treatment by injection has clear limitations.

SUMMARY OF THE INVENTION

In the present invention, a process is provided by which the absorption into the blood stream of vitamin B-12 taken orally is increased significantly. Surprisingly, such increased effectiveness has been obtained by administering vitamin B-12 sublingually in the form of a micro-lozenge containing cyanocobalamin or hydroxocobalamin. By utilizing this process, it has been found in tests to the present that there has been an average increase in serum B-12 levels in the 90% range.

DESCRIPTION OF PREFERRED EMBODIMENTS

As indicated above, the process of the present invention utilizes vitamin B-12 in the form of sublingual micro-lozenges. As will be described in more detail, the micro-lozenges are small in size, approximately ¼ inch in diameter, are easily dissolvable (approximately 4 minutes or less) and, in contrast to oral vitamin B-12 which has a tart and bitter quality, are pleasant tasting but without containing sugar. Typically, the lozenges contain 1,000 micrograms of vitamin B-12 which is equivalent to the dosage received in a single injection, although lesser or greater concentrations may be provided in the lozenges if desired. The vitamin B-12 may be either cyanocobalamin or hydroxocobalamin, with crystoline cyanocobalamin being particularly preferred because of its greater stability.

In a preferred formulation, the micro-lozenges comprise approximately 1,000 micrograms of vitamin B-12 blended with a carrier such as the alcohols mannitol or sorbitol and a lubricant such as magnesium stearate or a hydrogenated vegetable oil. The formulation also preferably contains a flavoring agent. Optionally, the formulation may also contain polyethylene glycol as an aid in granulating to form the lozenges and alginic acid or other equivalent ingredient to help in the disintegration of the lozenge when taken sublingually. The percentages of the ingredients of the formulation may vary depending upon the concentration of B-12 required, as indicated previously. Thus, in general, on a percentage by weight basis, the B-12 may be in the range of about 0.1 to approximately 10%, preferably about 0.5%, the lubricant from about 0.1 to about 5%, the carrier from about 85 to about 99.8%, and the flavoring agent, alginic acid and polyethylene glycol each about 0.1 to approximately 5%. An illustrative micro-lozenge formulation is thus:

Sorbitol—130 milligrams
Mannitol—43.5 milligrams
Polyethylene glycol—2 milligrams
Alginic acid—0.5 milligrams
Magnesium stearate—2.7 milligrams
Wild cherry flavor—1 milligram
Vitamin B-12—1 milligram In formulating the lozenges, the vitamin B-12, the alcohol and the polyethylene glycol (if included) are granulated with denatured ethyl alcohol (e.g. 5% methyl alcohol) to dissolve the vitamin B-12. This is then permitted to dry overnight at approximately 110° F., and is thereafter ground to approximately 16 mesh. The remaining ingredients are then dry blended into the dried 16 mesh material. The resulting blend is thereafter compressed in a standard tableting machine to provide micro-lozenges approximately ¼" in diameter and approximately three to five Strong Cobb units of hardness. Alternatively, the vitamin B-12 dissolved in alcohol as described above may be used to wet the dry carrier and other remaining ingredients, and the wetted mass then molded into the triturate form of micro-lozenge. To determine the effectiveness of the vitamin B-12 micro-lozenges, twenty human patients were selected, four of whom served as a control group and did not receive treatment with the sublingual vitamin B-12 micro-lozenges. The control group population was equally divided between male and female. All twenty patients had blood drawn for vitamin B-12 levels prior to commencement of the treatment procedure.

The sixteen patients not comprising the control group were given sublingual vitamin B-12 micro-lozenges of approximately the foregoing formulation containing 1,000 micrograms of crystalline cyanocobalamin three times a day for a testing period of seventeen days. These patients also received 800 micrograms of folic acid each day. Following the period of administration of the lozenges, blood levels were again drawn and examined. The results of these tests are set forth in the following table.

TABLE I

| Patients Tested | B-12 Level Before | B-12 Level After | % Increase |
|---|---|---|---|
| #1 | 900 PG/ML | 1490 PG/ML | +65.5% |
| #2 | 350 PG/ML | 940 PG/ML | +171.4% |
| #3 | 250 PG/ML | 940 PG/ML | +276.0% |
| #4 | 950 PG/ML | 1000 PG/ML | +5.0% |
| #5 | 456 PG/ML | 600 PG/ML | +31.9% |
| #6 | 995 PG/ML | 1080 PG/ML | +8.5% |
| #7 | 450 PG/ML | 1400 PG/ML | +211.0% |
| #8 | 350 PG/ML | 810 PG/ML | +131.4% |
| #9 | 450 PG/ML | 1350 PG/ML | +200.0% |
| #10 | 900 PG/ML | 1500 PG/ML | +66.7% |
| #11 | 550 PG/ML | 740 PG/ML | +34.5% |
| #12 | 700 PG/ML | 1465 PG/ML | +109.3% |
| #13 | 650 PG/ML | 1180 PG/ML | +81.5% |
| #14 | 950 PG/ML | 989 PG/ML | +4.1% |
| #15 | 600 PG/ML | 740 PG/ML | +18.9% |
| #16 | 850 PG/ML | 1130 PG/ML | +32.8% |
| CONTROL GROUP: None of these patients were given B-12 lozenges | | | |
| #17 | 1000 PG/ML | 650 PG/ML | −35.0% |
| #18 | 400 PG/ML | 450 PG/ML | +12.5% |
| #19 | 500 PG/ML | 360 PG/ML | −28.0% |
| #20 | 400 PG/ML | 260 PG/ML | −35.0% |

The Norm for This Blood Test is from 200 to 850 pg per Milliliter and the Assay Method Used Was the Bio-Rad Cobalt 57

As is evident from the foregoing table, the administration of the sublingual vitamin B-12 lozenges resulted in a significant increase in the serum B-12 levels, an average increase of 90%, compared to a 19.1% decrease among the control group. When viewed in light of the previously reported, blood absorption rate of only 1.2% for oral vitamin B-12, the results demonstrate the significantly effective administration of vitamin B-12 by use of the process of the present invention utilizing sublingual vitamin B-12 micro-lozenges.

Although the mechanisms by which the vitamin B-12 micro-lozenges function are not as yet totally understood, it is believed that the vitamin B-12 is quickly taken into the buccal membrane, lingual and sublingual arteries and veins, and is made available within the body in a dissolved form whereby it is effectively absorbed into the blood stream.

I claim:

1. A process for enhancing the absorption of Vitamin B-12 into the bloodstream, comprising administering Vitamin B-12 sublingually as a micro-lozenge containing from about 0.1% to about 10% by weight cyanocobalamin or hydroxocobalamin.

2. The process of claim 1 in which said micro-lozenge comprises about 0.1 to about 10 percent by weight crystalline cyanocobalamin or hydroxycobalamin, about 0.1 to about 5 percent by weight of a pharmacologically acceptable lubricant, and a pharmacologically acceptable carrier.

3. The process of claim 2 in which said lubricant is selected from the group consisting of magnesium stearate and hydrogenated vegetable oils.

4. The process of claim 2 in which said carrier is an alcohol.

5. The process of claim 4 in which said carrier is selected from the group consisting of mannitol and sorbitol.

6. The process of claim 2 in which said micro-lozenge additionally contains about 0.5 to about 5 percent by weight of alginic acid.

7. The process of claim 2 in which said micro-lozenge additionally contains a flavoring agent.

8. The process of claim 2 in which said micro-lozenge is dissolved under the tongue in approximately four (4) minutes or less.

9. A process for enhancing the absorption of Vitamin B-12 into the bloodstream, comprising administering Vitamin B-12 sublingually as a micro-lozenge comprising from about 0.1% to about 10% by weight crystalline cyanocobalamin or hydroxocobalamin, about 0.1% to about 5% of a lubricant selected from the group consisting of magnesium stearate and hydrogenated vegetable oils, and a pharmacologically acceptable carrier.

10. The process of claim 9 in which said micro-lozenge additionally contains about 0.5 to about 5 percent by weight of alginic acid.

11. The process of claim 10 in which said carrier is selected from the group consisting of mannitol and sorbitol and said micro-lozenge additionally contains about 0.1 to approximately 5 percent by weight of a flavoring agent.

12. A micro-lozenge composition for introducing Vitamin B-12 sublingually into the bloodstream comprising about 0.1 to about 10 percent by weight of crystalline cyanocobalamin or hydroxocobalamin, about 0.1 to about 5 percent by weight of a lubricant selected from the group consisting of magnesium stearate and hydrogenated vegetable oils, approximately 0.1 to about 5 weight percent alginic acid, approximately 0.1 to about 5 weight percent polyethylene glycol and a pharmacologically acceptable carrier.

13. The composition of claim 12 in which said micro-lozenge additionally contains about 0.1 to approximately 5 percent by weight of a flavoring agent and said carrier is selected from the group consisting of mannitol and sorbitol.

* * * * *